(12) United States Patent
Cesarczyk

(10) Patent No.: US 6,821,788 B2
(45) Date of Patent: Nov. 23, 2004

(54) DIAGNOSTIC TESTING DEVICE AND METHOD OF USE THEREOF

(75) Inventor: Edward Cesarczyk, North Easton, MA (US)

(73) Assignee: Avitar, Inc., Canton, MA (US)

( * ) Notice: Subject to any disclaimer, the term of this patent is extended or adjusted under 35 U.S.C. 154(b) by 0 days.

(21) Appl. No.: 09/778,125

(22) Filed: Feb. 6, 2001

(65) Prior Publication Data

US 2002/0106809 A1 Aug. 8, 2002

(51) Int. Cl.[7] .............................................. G01N 33/48
(52) U.S. Cl. ..................... 436/165; 422/61; 422/100; 422/58; 436/169
(58) Field of Search .......................... 422/58, 61, 100, 422/101; 436/165, 169, 177, 178, 180

(56) References Cited

U.S. PATENT DOCUMENTS

| 4,123,224 A | 10/1978 | Givner et al. ................. 422/59 |
| 4,963,325 A * | 10/1990 | Lennon et al. ................ 422/61 |
| 5,000,193 A | 3/1991 | Heelis et al. ................ 128/760 |
| 5,022,409 A | 6/1991 | Goldstein et al. ........... 128/760 |
| 5,169,789 A | 12/1992 | Bernstein .................... 436/501 |
| 5,260,031 A | 11/1993 | Seymour ..................... 422/101 |
| 5,268,148 A | 12/1993 | Seymour ..................... 422/101 |
| 5,283,038 A | 2/1994 | Seymour ..................... 422/101 |
| 5,339,829 A | 8/1994 | Thieme et al. .............. 128/760 |
| 5,376,337 A | 12/1994 | Seymour ..................... 422/101 |
| 5,380,492 A | 1/1995 | Seymour ..................... 422/101 |
| 5,393,496 A | 2/1995 | Seymour ..................... 422/101 |
| 5,479,937 A | 1/1996 | Thieme et al. .............. 128/760 |
| 5,494,646 A | 2/1996 | Seymour ..................... 422/101 |
| 6,150,178 A * | 11/2000 | Cesarczyk et al. .......... 436/165 |
| 2002/0004019 A1 * | 1/2002 | Bachand et al. ............. 422/58 |

* cited by examiner

Primary Examiner—Lyle A. Alexander
(74) Attorney, Agent, or Firm—George W. Neuner; Edwards & Angell LLP (57) ABSTRACT

A specimen collecting and testing device has a housing containing a test membrane. An elongated handle having a foam member is slidably received in the housing. Once the foam member obtains a specimen, the specimen is expelled from the foam member and delivered to a fluid chamber positioned along the test membrane. The device is then positioned horizontally and specimen that collects in the fluid chamber passes through an aperture in the fluid chamber and onto the test membrane located beneath the aperture. The test membrane may then be observed for optical changes in the case of an instant-type test, or removed for further processing. The device is particularly useful for collecting samples of urine or oral fluid for use in drug testing, pregnancy testing and the like; for testing of specimen for any of a variety of analytes such as HIV, hepatitis B, hepatitis C, etc.; and, for collecting samples of DNA for PCR testing.

34 Claims, 7 Drawing Sheets

DIAGNOSTIC TESTING DEVICE AND METHOD OF USE THEREOF

FIELD OF THE INVENTION

The present invention is related to devices for the collection of specimen, e.g., oral fluid, urine, or the like, and to diagnostic testing. The device of the present invention provides an absorbent foam member on a handle, and a housing for delivering the fluid specimen from the foam member onto a test membrane. More specifically, the device further includes a fluid chamber, within the housing, into which the fluid specimen from the foam member is deposited. The specimen that collects in the fluid chamber passes through an aperture in the fluid chamber and onto the test membrane located beneath the aperture. If the capacity of the fluid chamber is exceeded, the excess specimen may flow into a backup chamber where it may be retained or reabsorbed by the foam member. The device is particularly useful for the collection and testing of a specimen from a mammal while maintaining aseptic conditions.

BACKGROUND OF THE INVENTION

Various methods and devices have been used to collect and deliver specimen for diagnostic testing. One conventional method for collecting an oral fluid specimen is to use a cotton swab. The oral fluid sample can then be applied to a test device by contact with the swab or the sample can be rinsed from the swab.

Various devices comprising test tube like structures with sample absorbing means have been described for collecting biological samples for diagnostic testing. Examples of such devices are described in U.S. Pat. Nos. 4,123,224, 5,000,193, 5,022,409, 5,260,031, 5,268,148, 5,283,038, 5,339,829, 5,376,337, 5,380,492, 5,393,496, 5,479,937 and 5,494,646.

In a copending application, U.S. Ser. No. 08/712,682, a simple device for collecting and delivering a specimen for diagnostic testing is described. In accordance with the disclosure, a specimen collecting device comprises an elongated foam member having a longitudinal axis and an uncompressed cross sectional area, the elongated foam member being circumscribed by a hollow tubular member along a portion of the longitudinal axis, the hollow tubular member having a cross sectional area less than the uncompressed cross sectional area of the foam member so that the foam member is compressed along the circumscribed portion.

In another copending application, U.S. Ser. No. 08/869,105, filed Jun. 4, 1997, now U.S. Pat. No. 5,922,614 an improved device for collecting and delivering a specimen for diagnostic testing is disclosed, wherein the device provides a simple and convenient method for extracting the sample from a foam member. According to the disclosure, an embodiment of a specimen collecting device includes an elongated foam member having a longitudinal axis and an uncompressed cross sectional area, the elongated foam member being circumscribed by a hollow tubular member along a portion of the longitudinal axis, the hollow tubular member having a cross sectional area less than the uncompressed cross sectional area of the foam member so that the foam member is compressed along the circumscribed portion. Around the hollow tubular member is a flexible sleeve member having a first end that fits snugly around the hollow tubular member and a second end with an enlarged diameter that can surround the uncompressed foam member. Conveniently, the sleeve member can be moved along the hollow tubular member to cover and uncover the portion of the foam member that is not circumscribed by the hollow tubular member. Further, by sliding the flexible sleeve member along the hollow tubular member to cover the foam member and by squeezing the foam member through the flexible sleeve member, a portion of the fluid absorbed by the foam may be extracted.

SUMMARY OF THE INVENTION

The present invention provides a simplified and improved device for the collecting and diagnostic testing of a specimen. In particular, the present invention provides a simple and convenient method and device for obtaining a specimen sample on a foam member and testing the sample by delivering the sample to an integral diagnostic test membrane held within the device.

In accordance with the present invention, a specimen collecting and testing device comprises an elongated handle member having a foam member at an end thereof. The handle member is slidable within a hollow, elongated housing member, which holds the test membrane in a stationary position so that the specimen can be expressed from the foam member and deposited onto the test membrane. The foam member is positioned outside the housing member for sample gathering. Once the specimen has been collected by the foam member, the device is held vertically with the foam member pointing upwards. The handle member is then drawn downwards, thereby drawing the foam member into and through the housing member. As the foam member is drawn through the housing, the foam member expels specimen, which travels downwards by gravitational forces into a fluid chamber located within the housing. The device is then held horizontally or placed horizontally on a surface and the specimen is deposited onto the test membrane to react with the test chemistry carried thereby.

According to one embodiment, the foam member comprises a material which, when wetted by the sample specimen, will expand from its dry configuration and, when compressed, will express specimen.

In one embodiment, the foam member, when wetted, will have a cross sectional area that is greater than at least a portion of the housing member such that, when the handle member is drawn through the housing member, the foam member is compressed, thereby expressing specimen into the fluid chamber.

In another embodiment, after specimen has been collected in the foam member, the device is held vertically with the foam member pointing upwards as the foam member is drawn through the housing member. A barrier located proximate the fluid chamber compresses the foam member as the foam member passes through the housing member. The compression of the foam member expresses specimen, which is deposited into the fluid chamber. The device is then positioned horizontally and the specimen in the fluid chamber passes through an aperture in the fluid chamber onto the test membrane.

Preferably, a backup chamber is located next to the fluid chamber such that if the fluid chamber's holding capacity is exceeded, the excess specimen flows into the backup chamber where it may be retained or reabsorbed by the foam member. Thus, if a large amount of specimen is absorbed into the foam member, it may be expelled from the foam member into the fluid chamber and excess will then flow into the backup chamber to prevent excess specimen from being deposited onto the test membrane, which may negatively impact test results in some cases.

In a particularly preferred embodiment, the fluid chamber is designed to have a specimen holding capacity corresponding to particular volumes of specimen required for various specimen tests. If the specimen holding capacity is exceeded, the excess specimen will flow into the backup chamber, as described in more detail below.

In one embodiment, the foam member has a longitudinal axis and an uncompressed cross sectional area. The elongated foam member is circumscribed by a hollow, elongated handle along a portion of the longitudinal axis. In one embodiment, at least one portion of the hollow, elongated handle has an interior cross sectional area that is less than the uncompressed cross sectional area of the foam member, so that the foam member is compressed to deliver the sample to the fluid chamber located inside the hollow, elongated housing.

The diagnostic testing device of the present invention is particularly useful for collecting a sample of a fluid specimen and delivering the sample to a test membrane for a rapid one-step drugs of abuse test. It can also be used to provide fluid samples, particularly oral fluid or urine samples, for DNA testing for forensic and paternal identification, RNA testing, antibody testing, testing for disease, and other similar diagnostic procedures. The testing device of the present invention provides a simple and inexpensive method for collecting and testing the oral fluid sample. Further, in preferred embodiments of the invention, the foam member and fluid chamber of the diagnostic testing device will provide more consistent and accurate samples and test results.

DETAILED DESCRIPTION OF THE INVENTION

Referring now to the various figures of the drawings wherein like reference characters refer to like parts, there is shown in FIGS. 1–7 various views of a diagnostic testing device in accordance with one embodiment of the invention.

Figure 1:
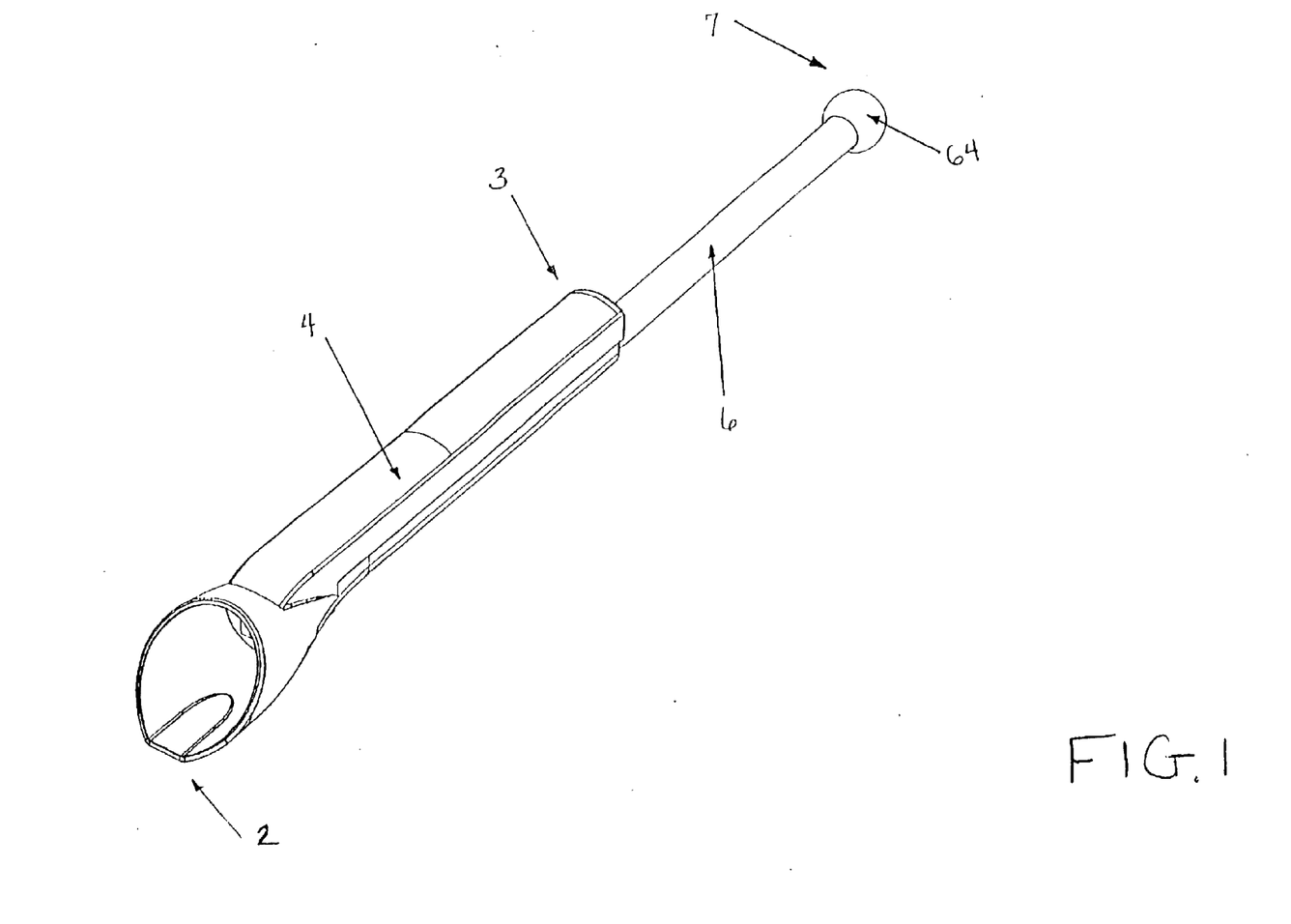
FIG. 1 is a top perspective view of the diagnostic testing device in accordance with an embodiment of the present invention illustrating the configuration of the device during delivery of a specimen to the test membrane in the housing.
Figure 2:
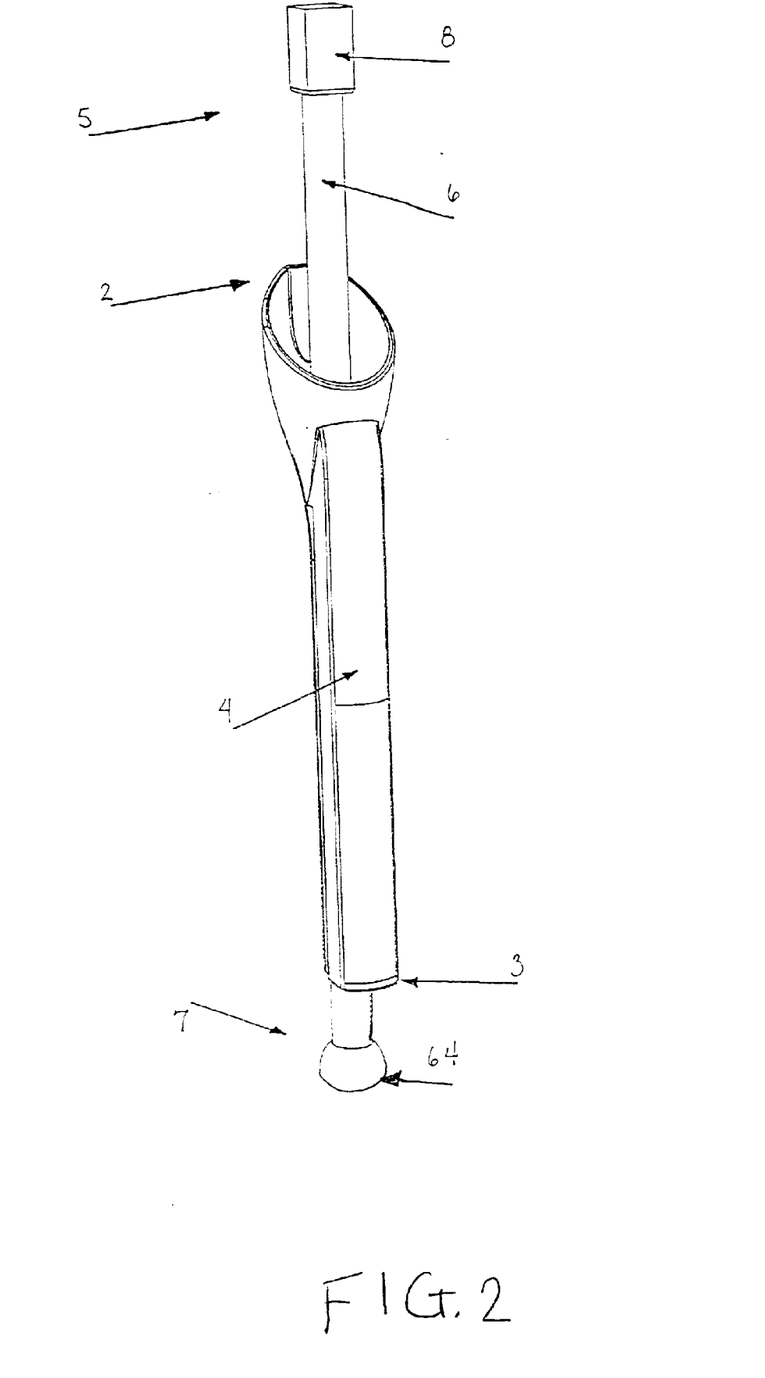
FIG. 2 is a perspective view of the diagnostic testing device of FIG. 1, illustrating the vertical configuration of the device during specimen collection and prior to delivery of the specimen to the test membrane in the housing.
Figure 3:
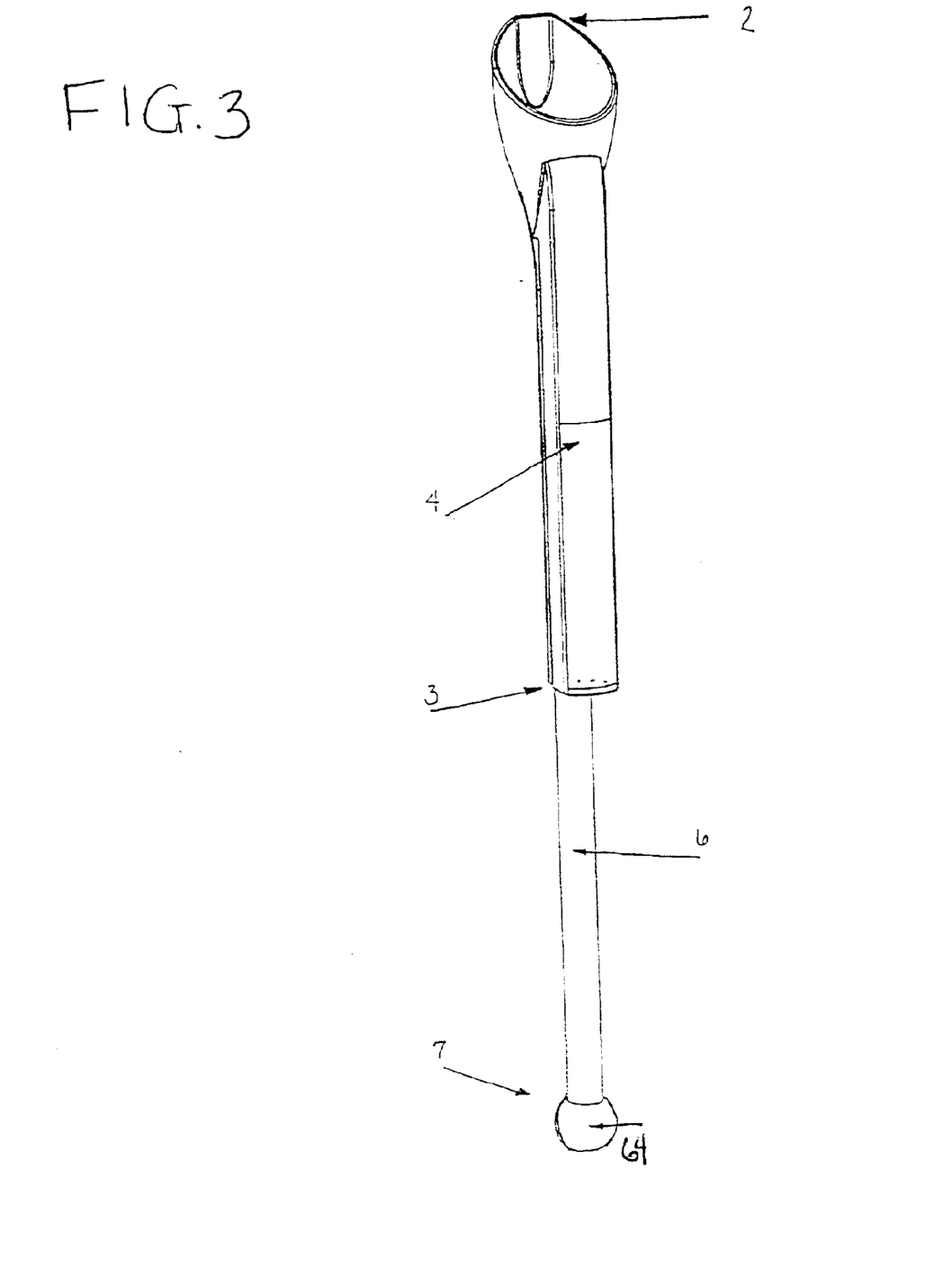
FIG. 3 is a perspective view of the diagnostic testing device of FIG. 1, illustrating the vertical configuration of the device during delivery of a specimen to the test membrane in the housing.

The diagnostic testing device comprises an elongate membrane housing 4 and an elongate handle 6 received inside the membrane housing 4. As illustrated in FIGS. 1–3, the handle 6 is slidably received inside the membrane housing 4 and is dimensioned so as to slide within the membrane housing 4 without interference.

The membrane housing 4 has a proximal end 2 and a distal end 3, and the handle 6 has a proximal end 5 and a distal end 7. Preferably, the membrane housing 4 has a substantially constant cross section along its length. As shown in FIGS. 1–6, in some embodiments the membrane housing 4 may have an enlarged proximal end 2 through which the handle 6 and foam element 8 can pass without interference. The proximal end 2 of the membrane housing 4 can be equipped with a tamper-proof seal (not shown) to provide indicia that the device has not been opened or used.

As shown in FIG. 2, a foam element 8 protrudes from the proximal end 5 of the handle 6 a certain distance for collecting a specimen. On the distal end 7 of the handle 6, opposite the foam element 8, the handle 6 may optionally receive an end cap 64, which provides a convenient gripping point for the user. The end cap 64, if desired, can be fabricated of a rubber or similar material to enhance gripping ability or it may include ridges or similar grip enhancing means.

In one embodiment, the foam element 8 is mounted on the proximal end 5 of the handle 6 using adhesive or other kinds of retainers. In a particularly preferred embodiment, the handle 6 is partially or wholly hollow and the foam element 8 is held and retained within the handle 6. The foam is compressible, and preferably, in its uncompressed state, it has a cross section greater than the inside cross section of the hollow portion of the handle 6 such that a portion of the foam element 8 is held within the hollow handle 6 without requiring adhesive or other kinds of retainers. As such, during assembly, the foam element 8 is compressed along its longitudinal axis and extruded or otherwise introduced into the handle 6, where it is circumscribed thereby. Alternatively, the foam element 8, in its uncompressed state, may have a cross section less than or equal to the cross section of the hollow portion of the handle 6 and adhesives or other kinds of retainers are used to hold the foam element 8 within the handle 6.

The protruding volume of the foam element 8 is the primary location for absorption of a fluid sample for delivery to the test membrane and subsequent testing. The protruding volume of the foam element 8 is selected depending upon the type of fluid being sampled and the volume of fluid required for a particular diagnostic test. Generally, the foam element 8 will protrude from the end of the handle 6 a distance equal to about 25% to about 400% of the mean diameter of the handle 6 or the mean diameter of the uncompressed cross section of the foam element 8. If the handle 6 or foam element are not circular, the largest dimension of the cross section can be used to approximate the mean diameter for this purpose. Alternatively, the foam element 8 will generally protrude a distance of about 0.125 inch to about 2 inches from the end of the handle 6, depending upon the diameter of the handle 6. Preferably, the foam element 8 protrudes from the handle 6 a distance of one to three times the mean diameter of its uncompressed cross section for oral fluid collection, and about one to two times the mean diameter for urine collection.

To collect a sample using any of the described embodiments, a liquid sample, e.g., oral fluid or urine, or the like, can be collected by wicking the fluid into the foam member, e.g., in as little as 15 seconds, by touching the foam member to a liquid specimen.

In one preferred embodiment, the foam element 8 extends into a hollow portion of the handle 6 for a sufficient distance to be retained in the handle 6. Generally, the foam element 8 should extend into the handle 6 a distance at least equal to the diameter of the handle's cross-section. For certain embodiments, the foam element 8 preferably should extend into the handle 6 a distance at least equal to the length of the foam protruding from the handle 6. Of course, the foam can extend the full length of the handle 6 if desired.

The foam element 8 can be made of a variety of absorbent foams. Preferably, the foam is formed and cut to the desired size to expose the cell structure rather than a molded foam part having a surface skin. Preferred materials for the foam member include, e.g., polyurethane foam, polyethylene foam, polyvinylchloride foam, ethylvinylacetate foam, polyethylene/ethylvinylacetate foam, polyester foam and polyether foam. Absorbent Porex™, silicone and latex foams can also be used. Particularly useful foam for the collection of oral fluid is polyurethane foam sold under the mark HYDRASORB® by Avitar, Inc., Canton, Mass., USA. The preferred polyurethane foam has a uniform cell count of about 60 or more cells per linear inch. More preferably, the uniform cell count is about 80 to 120 cells per linear inch.

The handle 6 circumscribing the foam element 8 can be made of any suitable material having sufficient strength to compress and hold the foam element 8 and to be handled during collecting and delivery of the specimen. Typical materials suitable for the handle 6 include, for example, paper, polyethylene, polypropylene, polyester, vinyl and other plastics. A circular cross section for the handle 6 is shown in FIGS. 1 through 3, but other shaped cross sections, such as rectangular, triangular, pentagonal, etc., can also be used.

Materials useful for the membrane housing 4 can be the same as some materials useful for the handle 6. Preferably, the membrane housing 4 is fabricated of a moldable material, such as, for example, polyethylene, polypropylene, polystyrene, polyester, vinyl and the like. Any material can be used that has sufficient rigidity to maintain a shaped structure. The material preferably also is inert to a liquid sample for a sufficient time to complete testing. Those skilled in the art can readily select a suitable material from the wide variety of materials known for medical use and diagnostic testing.

Figure 4:
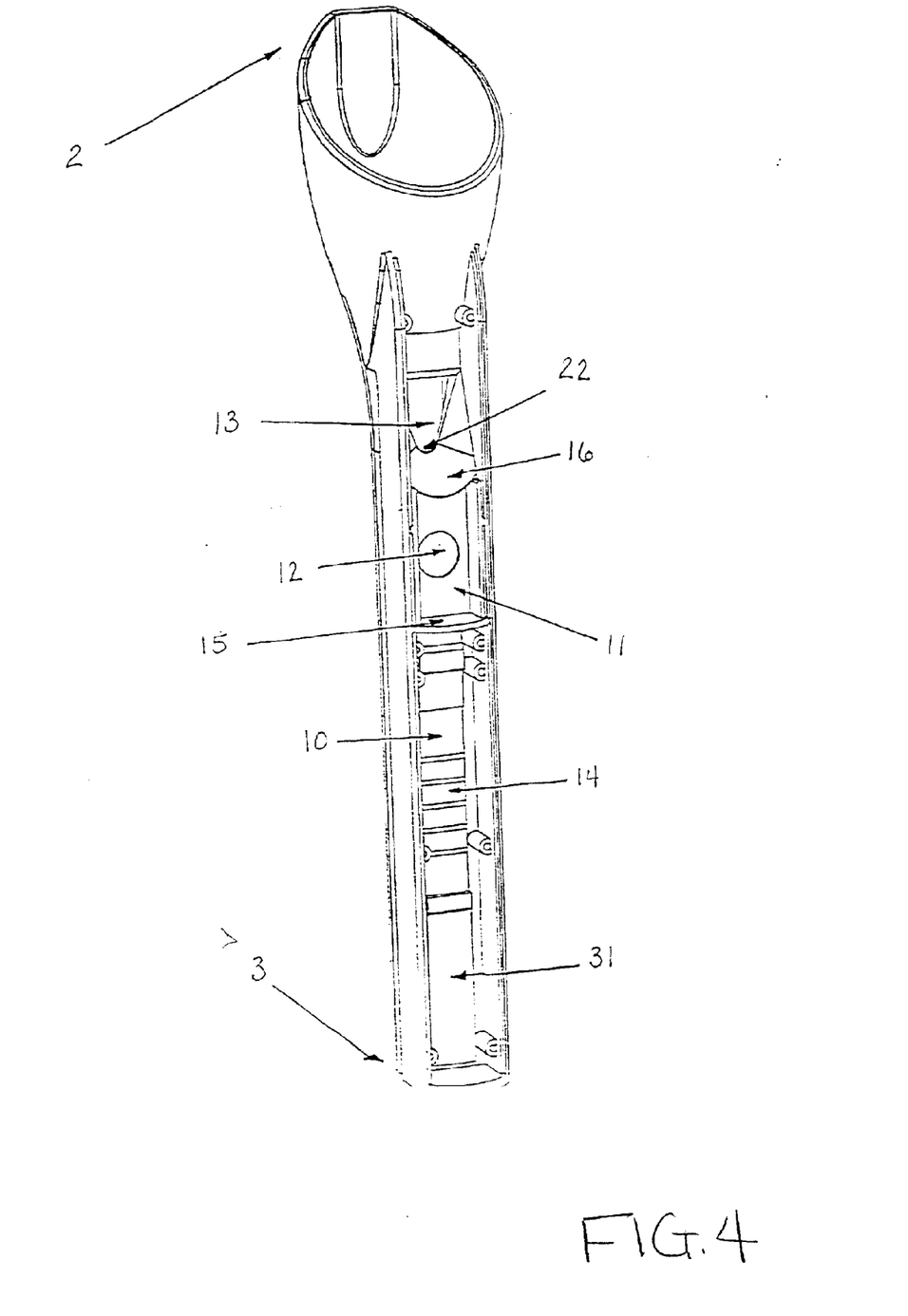
FIG. 4 is a perspective view of the diagnostic testing device in accordance with an embodiment of the present invention, wherein portions of the housing are removed to expose the interior of the housing.
Figure 5:
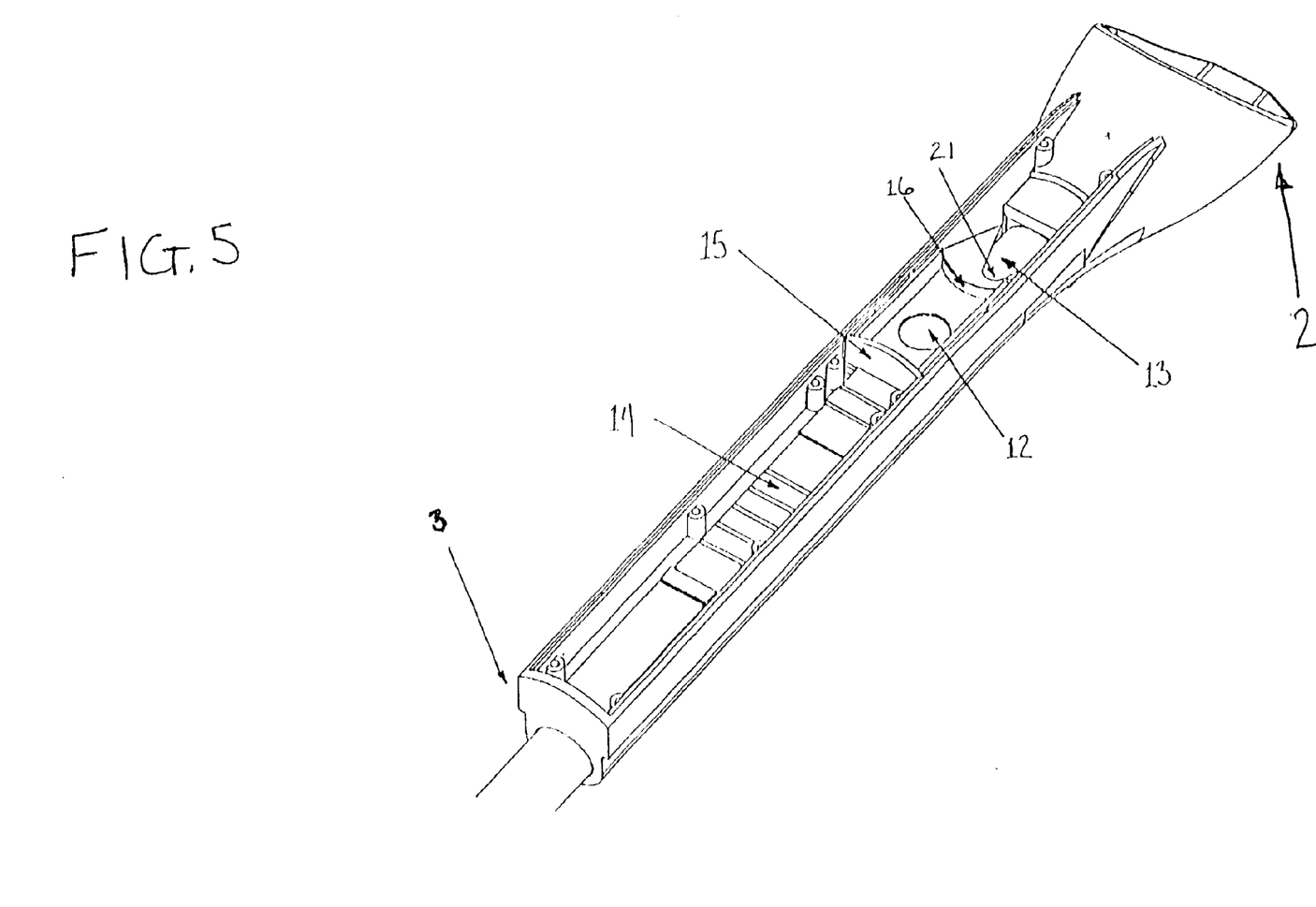
FIG. 5 is a top perspective view of the diagnostic testing device of FIG. 4 with portions of the housing removed to expose the interior of the housing.
Figure 6:
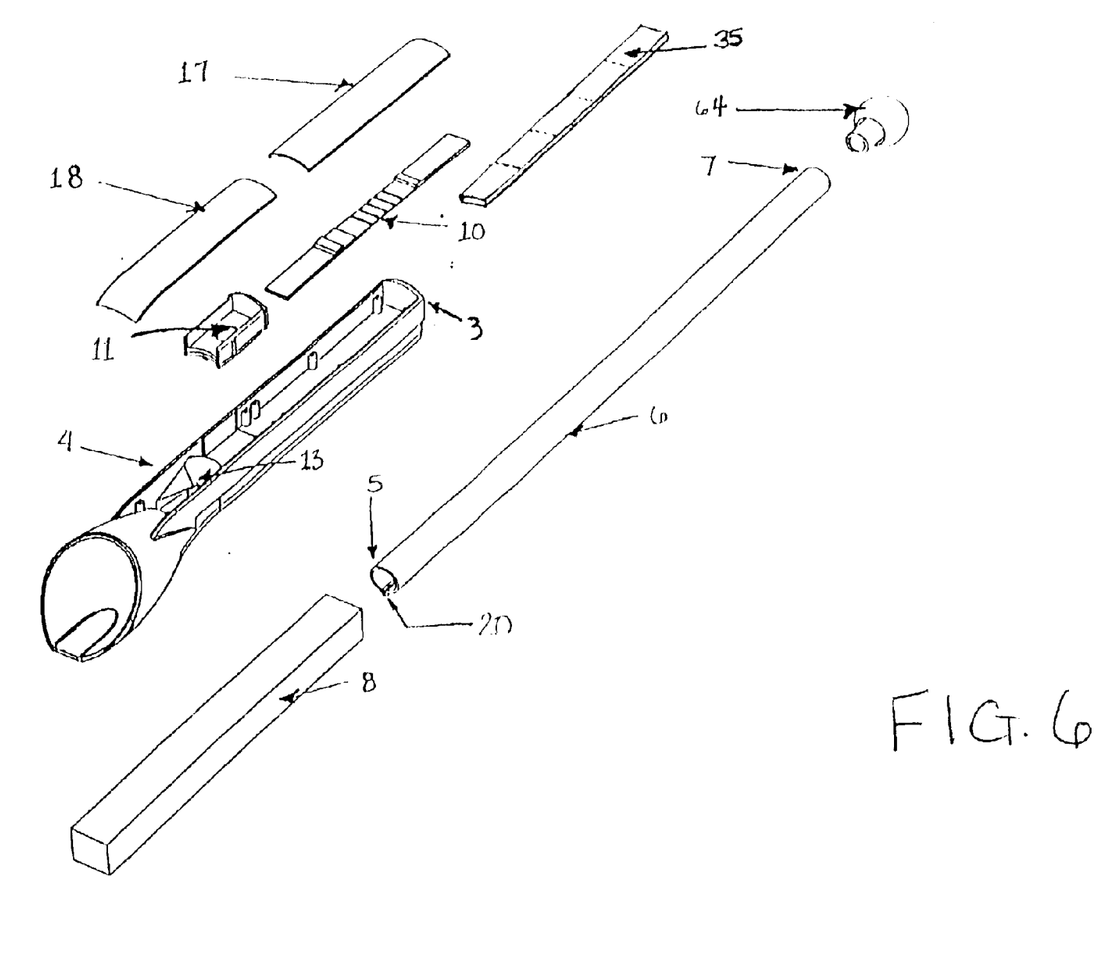
FIG. 6 is an exploded view showing the major components of an embodiment of the present invention.

As further seen in FIGS. 4–6, the device includes a test membrane 10 that is retained in the membrane housing 4 during delivery of the specimen. The test membrane 10 can be separated into discrete sections 14, each carrying diagnostic test chemistry, and a reagent zone 29. The chemistry when in contact with specimen, as elaborated upon hereinbelow, forms the basis of a diagnostic test. Suitable diagnostic test chemistries are well known to those skilled in the art to diagnose a wide variety of substances such as, for example, glucose, viruses, hormones, bacteria, alcohol, drugs of abuse, etc. Representative chemistries for the testing of glucose levels in whole blood are disclosed by Phillips in U.S. Pat. No. 4,935,346. Bronstein discloses in U.S. Pat. No. 4,978,614 chemistries for the detection of urinary components, and Zeng discloses test chemistries for detecting AIDS or other antibodies in EP 0 495 465. Generally, the preferred reagent will be a dry, immobilized chemistry, which is hydrated by incorporation of the liquid sample.

Figure 7:
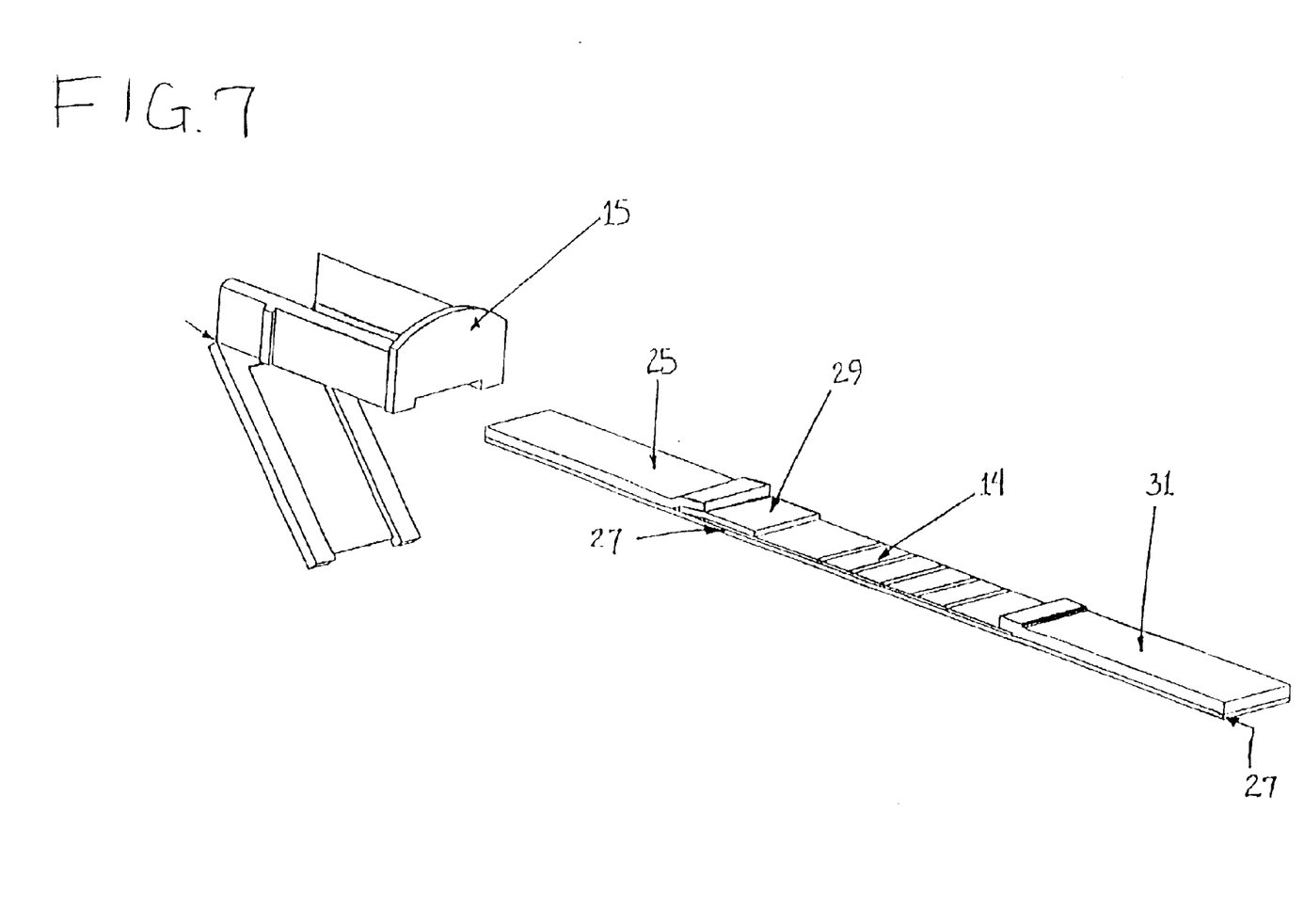
FIG. 7 is an exploded view showing the test membrane with membrane clip according to an embodiment of the present invention.

Preferably, the micropore size of the test membrane 10 will be in the range of about 0.05 microns to about 30 microns, and more preferably in the range of about 0.1 microns to about 20 microns. A liquid sink zone 31 (see FIG. 4) preferably is provided on the test membrane 10 for absorbing excess liquid that is conducted by capillary action through the length of the test membrane 10. As shown in FIG. 7, the test membrane 10 also includes a membrane support 27 for integrally supporting the sample receiving zone 25, the reagent zone 29, the sections 14 containing the test chemistries, and the liquid sink zone 31.

The test membrane 10 preferably comprises an elongate strip that is sized and shaped to fit within the membrane housing 4. As shown in FIGS. 4–5, the test membrane 10 is preferably positioned along a surface within the housing 4, where it preferably locks into place via a friction fit. Conventional retaining means such as adhesives or slot and tab arrangements (not shown) also can be used to assist in holding the test membrane in place within the membrane housing 4.

As shown in FIG. 2, after a specimen is collected by the foam element 8, the device is held vertically with the foam element 8 containing the specimen pointing upwards. As shown in FIG. 3, the handle 6 is then pulled downwards through the membrane housing 4, thereby drawing the foam element 8 through the membrane housing 4. As the foam element 8 is drawn through the membrane housing 4, it is compressed to expel specimen.

After specimen has been expelled from the foam element 8, the device is then positioned horizontally, as shown in FIG. 1. When the device is positioned horizontally, the fluid chamber 11 is positioned above the test membrane 10, preferably above the sample receiving zone 25 which is at the proximal end 2 of the test membrane 10. An aperture 12 in the fluid chamber is positioned above the test membrane 10. When the device is positioned horizontally, the specimen in the fluid chamber 11 passes through the aperture 12 onto the test membrane 10.

In one embodiment, the fluid chamber 11 is removably mounted on a proximal end portion of the test membrane 10, as shown in FIGS. 6 and 7. For example, as shown in FIG. 7, the fluid chamber 11 can have a hinge 19 or the like so that it can be removably clipped or attached to the test membrane 10. The test membrane 10 and fluid chamber 11 then is placed into the housing 4 and retained by a frictional fit and/or fastening means such as slot and tab arrangements or adhesives (not shown).

Preferably, the housing 4 has at least one portion positioned above the test membrane 10 position that is made of a transparent or similar material. For example, the membrane chamber cover 17 and/or fluid chamber cover 18 can form the transparent portion above the test membrane 10. Alternatively, the portion of the housing, which is positioned above the test membrane 10, has an opening or window to permit observation of the test membrane. In such an embodiment, it is further preferred that the opening or window is designed such that the test membrane 10 can be removed from the housing through the opening or window.

In some embodiments, a sample collecting strip 35 alternatively can be used in the housing 4 in place of the test membrane 10, to collect specimen. As shown in FIG. 6, the sample collecting strip 35 is inserted and retained in the membrane housing 4 during delivery of the specimen. The sample collecting strip 35 normally carries no diagnostic test chemistry, can be perforated or otherwise separated into discrete sections, and is typically used to collect an amount of specimen. Sample collecting strips are well known and, thus, although described and shown with reference to a preferred embodiment, the general features (e.g. size, shape, materials, number and sizes of perforations) of the sample collecting strip 35 is in accordance with conventional sample collecting strips. In FIG. 6 the sample collecting strip 35 is shown with four perforations spaced equidistant from each other. However, the sample collecting strip 35 can have any number of perforations spaced equidistant or at varying distances from each other. After the sample collecting strip 35 has collected an amount of specimen, the sample collecting strip 35 can then be removed from the membrane housing 4 for further tests such as, e.g., gas chromatography or mass spectrometry testing. In some applications, sample preservation is important. For example, in a case where a specimen such as saliva is collected and transported to a testing facility, the sample must be preserved until it is tested. Thus, sample preservation means are preferably utilized. In one preferred embodiment, the sample collecting strip 35 is impregnated with preservatives such as sodium benzoate and/or citric acid, which aid in preserving the specimen.

As shown in FIG. 6, the housing preferably is fabricated to have a removable membrane chamber cover 17 and fluid chamber cover 18. Alternatively, a single removable cover rather than the two separate covers 17, 18 can be utilized. The cover(s) 17, 18 may be completely removable or may be, for example, attached with hinges or the like such that the covers swing open and provide access to the interior of the housing 4 and to provide the user with a view of the test membrane 10 and interior of the housing. In some embodiments, the housing 4 is formed without any removable covers or portions. For example, in one embodiment, the portions of the housing above the test membrane 10 and/or the fluid chamber 11 are left open without any covers, or have covers with partial openings, so that the user has immediate access to the interior of the housing 4 and so that the user can view the test membrane 10 and interior of the housing. In a preferred embodiment, the portions of the membrane housing 4 located above the test membrane 10 and/or the fluid chamber 11 are fabricated of a material that allows a user to see the test membrane 10 and/or fluid chamber 11 within the housing 4. In one embodiment, if desired, the entire membrane housing 4 or a substantial portion of the membrane housing is fabricated of a material that allows a user to see the interior of the housing 4.

FIG. 2 shows the device primed for delivery of the specimen-containing foam element 8 to the test membrane 10 in the membrane housing 4. It is pointed out that, in this illustrative embodiment, saturation of the foam element 8 causes it to expand beyond its uncompressed dry cross-sectional dimension. After specimen is collected by the foam element 8, the device is held vertically with the foam element 8 pointing upwards. The handle is then pulled downwards through the membrane housing 4, thereby pulling the foam element 8 downwards through the membrane housing 4. As shown in FIG. 2, the handle 6 typically is retained within the membrane housing 4 during specimen collection. The handle 6 also can be retained within the membrane housing 4 after the specimen has been deposited into the fluid chamber. The handle 6 can be held in the membrane housing 4 by any conventional means, including a locking tab detent and locking tab arrangements (not shown). Alternatively, in some embodiments, the handle 6 with foam element 8 can be used alone to collect specimen and the handle subsequently can be introduced into the membrane housing 4 after the foam element 8 has been saturated with specimen.

FIGS. 1–3 depict the sequence of device configurations during the delivery of specimen to the fluid chamber 11 and test membrane 10. After the specimen has been collected by the foam element 8, the device is first held vertically with the foam element 8 pointing upwards (FIG. 2) and, as the handle 6 is pulled downwards through the membrane housing 4 the foam element 8 passes through the membrane housing 4 (FIG. 3). The foam element 8 enters a compression area where the foam element 8 is compressed to expel specimen, which flows downwards into the fluid chamber 11. Preferably, the foam element 8 is compressed when it contacts a first barrier 16 located at the proximal end of the fluid chamber 11. In a preferred embodiment, a compression area assists in extracting specimen of various viscosities from the foam member. The compression area can be of any shape, for example, it can be V-shaped, U-shaped, straight, flat or chamfered. As shown in FIGS. 4 and 5, for example, a "V"-shaped or "U"-shaped configuration 22 of the leading edge of barrier 16 is used to form a U-shaped or V-shaped compression area that assists in the extraction of specimen from the foam element 8. A second barrier 15 is further located on the distal end of the fluid chamber 11 so as to prevent specimen from flowing past the fluid chamber 11 onto the test membrane 10. The device is then positioned horizontally, preferably by placing the device on a level surface, and the specimen in the fluid chamber 11 levels off and flows through the aperture 12 onto the test membrane 10 to contact the test chemistries. Excess specimen can flow into the backup chamber 13 to prevent excess specimen from being deposited onto the test membrane 10. To prevent the device from rolling when placed on the level surface, the housing 4 preferably has an outer surface with at least one flat area.

The handle 6 can be retained within the membrane housing 4 during the delivery of the specimen to the fluid chamber 11. For example, the handle 6 can be held in the membrane housing 4 by any conventional means, including a locking tab detent and locking tab arrangement (not shown). In this type of an arrangement, the handle 6 is held in the membrane housing 4 so that the foam element 8 containing the fluid sample is held in the compression area where specimen is expelled.

A keyway 20, shown in FIG. 6, can be formed in the handle 6. The keyway 20 is designed so as to aid in maintaining the orientation of the foam element 8 and so as to aid in maintaining proper orientation of the locking tab detent with respect to the locking tab arrangement.

In one embodiment, the exposed portion of the dry foam member 8 has a reduced lateral cross sectional area (not shown), and is retained in the handle 6 by a frictional fit and/or through the use of adhesives or other known means. In this embodiment, the protruding portion of the foam member 8 is sized to expand when wet so that it undergoes little or no compression as it makes contact with and moves through the slid housing 4. Alternatively, the protruding portion of the dry foam member 8 can have a cross sectional area (not shown) that is larger than that of the portion of the foam member 8 disposed in the handle 6 and, when wet, is larger than at least a portion of the cross sectional area of the inside of the membrane housing 4. Again, the foam member 8 can be retained in the handle 6 by interference fit, or through the use of adhesives or other known means.

Preferably, a backup chamber 13 is located within the membrane housing 4 such that excess specimen from the fluid chamber 11 can pass into the backup chamber 13 for retention or for reabsorption by the foam member 8. In one preferred embodiment, as shown in FIGS. 4–5, the backup chamber 13 is located on the proximal side of the fluid chamber 11. If the fluid chamber 11 capacity is exceeded when the device is placed horizontally, excess specimen from the fluid chamber 11 passes into the backup chamber 13. This can be accomplished, for example, by providing a shorter barrier 16 in between the fluid chamber 11 and backup chamber 13 over which the excess specimen can flow or, for example, by providing fluid communication between the fluid chamber 11 and the backup chamber 13 that allows excess specimen to flow into the backup chamber 13.

FIG. 4 shows the handle 6 removed from the membrane housing 4 after delivery of specimen to the test membrane 10. At this point, the handle 6 is discarded. A locking tab or the like (not shown) mounted on the membrane housing 4 may be used to form a ratcheting mechanism with a locking tab detent or the like mounted on the handle 6, thereby preventing the handle 6 and foam member 8 from being reinserted into the membrane housing 4 and reused after the specimen has been delivered to the test membrane 10. In a preferred embodiment, the handle 6 locks into its proper position for specimen extraction and remains there.

In some embodiments, for tests such as drug testing, bacteriological testing, the testing of urinary ketones or simple pH testing, the results of the diagnostic test can be read directly on the test membrane 10 through a transparent membrane housing 4 or through transparent portions of the membrane housing 4, such as the membrane chamber cover 17 and/or fluid chamber cover 18, without the need of disassembling the device. Alternatively, the portion of the membrane housing 4 above the test membrane 10 can be removable or can be left open, such that the results of the diagnostic test on the test membrane 10 can be read directly through the opening in the membrane housing 4. For some tests, such as DNA tests or for confirmatory testing purposes, the membrane housing 4 can be mailed in a sealed container to a laboratory for additional processing and obtaining results.

FIG. 6 shows an illustrative embodiment of the present invention in an exploded view. The device comprises a housing 4 that receives in mating fashion a handle 6. The handle 6 has a cross section that is received in the distal end 3 opening of the housing 4 in a snugly fitting relationship. The foam member is mounted on the proximal end 5 of the handle 6. Preferably, at least a portion of the handle 6 is hollow, as shown in FIG. 6, and a portion of the foam member 8 is held within the handle 6. The distal end 7 of the handle 6 optionally can have a cap 64 mounted on it, which provides a convenient gripping point for the user. The handle 6 can have an internal bore (not shown) with a depth sufficient for receiving the cap 64, or the cap 64 can have an internal bore (not shown) designed to fit over and receive a portion of the handle 6. Alternatively, the handle 6 and the end cap 64 can be provided as one piece. The end cap 64 may be advantageously provided with texture gripping surfaces (not shown).

The diagnostic testing device of the present invention is particularly useful to provide liquid samples extracted from the foam for diagnostic analysis or identification of drugs, antibodies, DNA, RNA, and the like.

The diagnostic testing device of the present invention also is useful for collecting samples of oral fluid for subsequent isolation of DNA for PCR. After delivery of the specimen to the sample collecting strip 35, the sample is dried. The sample collecting strip 35 may be perforated, if desired, so that after collection of specimen, the sample collecting strip 35 can be broken apart for subsequent testing. DNA is isolated from the sample for analysis using a PCR technique (see, e.g., Cheng et al., *Proc. Natl. Acad. Sci. USA*. 91:5695–5699 or Wright et al., *J. Clin. Microbiol.* 32: 464–468). The collection matrix can be a conventional paper matrix or, preferably, a collection matrix sold under the brand name IsoCode™ by Schleicher & Schuell, Keene, NH 03431.

A particularly useful diagnostic membrane for the practice of the present invention is described in copending application Ser. No. 09/123,376 filed Jul. 27, 1998, the disclosure of which is hereby incorporated by reference. It describes a diagnostic test membrane comprising a porous membrane having a sample receiving zone containing a fatty acid sarcosinate surfactant, reagent chemistry including antibodies to a particular analyte that are freely mobile when the membrane is moist, and spaced from the sample receiving zone a detection zone for detecting the presence of said particular analyte, the detection zone containing immobilized molecules of said particular analyte that are not free to move when the membrane is moist. A detectable change is produced in the detection zone when antibodies bind to the immobilized analyte. Preferably the detectable change is a visible change, such as production of a color. Also preferably, a control zone is provided downstream of the detection zone, wherein the presence of the sample causes a detectable change, preferably a visible change. The detection of change in the control zone can denote the presence of sufficient sample in the diagnostic test membrane. A liquid sink zone can also be provided further downstream from the control zone, e.g., at an opposite end of the diagnostic test membrane from the sample receiving zone. Of course, the zones can also be constructed in annular rings around the sample receiving zone.

A microporous nitrocellulose layer is coated with stripes of suitable chemicals to provide the test zone and control zone. A layer of solution containing the appropriate chemicals is coated in the surface of the nitrocellulose in a stripe to form each zone. By controlling the amount of solution laid down, the width of the zones can be controlled with a suitable distance between the zones being devoid of chemicals. The coated layer is then dried, cut into the desired size. Any suitable membrane material can be used, for example, a $0.5\mu$ nitrocellulose microporous filter membrane.

A reagent zone is made by imbibing reagent chemicals into a fibrous polyvinyl or polyester filter layer to provide the appropriate concentration and drying the layer. Any suitable filter material can be used, for example, a $1.2\mu$ hydrophilized polypropylene filter material (SA3J853F0) sold by Millipore Corporation (Bedford, Mass.). After drying the reagents, the membrane is cut into the desired size and positioned on the nitrocellulose membrane.

The sample receiving zone is made by imbibing a solution containing a suitable buffer and a fatty acid sarcosinate into a sheet of non-woven material to provide the appropriate concentration. The buffer is selected for the analyte and specimen for which the test strip is designed. A preferred fatty acid sarcosinate is sodium myristoyl sarcosinate, which is provided at a concentration of about 1.0 wt %. The fatty acid sarcosinate surfactant can be obtained from Hampshire Chemical Corporation, which manufactures and sells such surfactants under the brand name Hamposyl. The surfactant sold as Hamposyl M30 is sodium myristoyl sarcosinate. Preferably, the fatty acid sarcosinate is present in the imbibing solution at a concentration of from about 0.1% to about 10% by weight. The sheet is dried, cut into the desired size and positioned adjacent the reagent zone. The non-woven material can be, for example, any conventional filter material such as 470 paper (Cat. No. 539929) or 740 paper (Cat. No. 539930), which are available from Schleicher and Schuell.

The bibulous matrix can be any of a variety of materials having a porous structure for absorption of aqueous fluids, for example, non-woven fibrous materials including paper and microporous polymer membranes including foam membranes.

The invention has been described in detail with reference to preferred embodiments thereof. However, it will be appreciated that, upon consideration of the present specification and drawings, those skilled in the art may make modifications and improvements within the spirit and scope of this invention as defined by the claims.

I claim:

1. A specimen collecting and testing device comprising:
    an elongate, hollow housing having a proximal end and a distal end and a hollow portion;
    at least one test membrane or sample collecting strip positioned within the hollow portion of the housing, the test membrane carrying diagnostic test chemistry;
    a fluid chamber, for holding specimen, positioned adjacent to the test membrane or sample collecting strip;
    at least one elongate handle member, having a proximal end and a distal end, slidably received in the hollow portion of the housing; and
    a foam member, for collecting specimen, extending from the proximal end of the handle whereby, when the handle is drawn through the housing, collected specimen is deposited from the foam member into the fluid chamber and onto the test membrane or sample collecting strip,
    wherein the housing includes a channel for receiving the handle member and foam member, and the fluid chamber is adjacent said channel.

2. The specimen collecting device of claim 1 further comprising an aperture in the fluid chamber through which specimen deposited in the fluid chamber passes onto the test membrane or sample collecting strip.

3. The specimen collecting and testing device of claim 1 further comprising a barrier or compression area on the proximal side of the fluid chamber, whereby, as the handle is drawn through the housing, the foam member contacts and is compressed by the barrier or compression area, thereby expelling specimen that is collected by the foam member into the fluid chamber.

4. The specimen collecting and testing device of claim 1, further comprising a barrier or compression area, whereby the barrier or compression area assists in extracting specimen or various viscosities from the foam member.

5. The specimen collecting and testing device of claim 4, wherein the barrier or compression area is V-shaped, U-shaped, straight, flat and/or chamfered.

6. The specimen collecting device of claim 1, further comprising a backup chamber, whereby specimen in excess to the capacity of the fluid chamber flows into the backup chamber.

7. The specimen collecting device of claim 1, wherein a barrier forms the distal side of the fluid chamber and prevents specimen deposited in the fluid chamber from flowing over or around the barrier onto the test membrane.

8. The specimen collecting device of claim 1 wherein a barrier forms the proximal end of the fluid chamber and is sized to meter the amount of specimen in the fluid chamber.

9. The specimen collecting and testing device of claim 1, wherein the elongate, hollow housing has an outer surface with at least one flat area, whereby, when the specimen collecting and testing device is placed on a surface, the at least one flat area prevents the specimen collecting and testing device from rolling.

10. The specimen collecting and testing device of claim 1, wherein the housing is made of plastic.

11. The specimen collecting and testing device of claim 1, wherein the foam member comprises a material selected from the group consisting of polyurethane foam, polyethylene foam, polyvinylchloride foam, ethylvinylacetate foam, polyethylene/ethylvinylacetate foam, polyester foam and polyether foam.

12. The specimen collecting and testing device of claim 11, wherein the foam member comprises a polyurethane foam.

13. The specimen collecting and testing device of claim 1, wherein the handle member is hollow.

14. The specimen collecting and testing device of claim 13, wherein a portion of the foam member is disposed in the hollow handle member.

15. The specimen collecting and testing device of claim 1, wherein the handle member is made of paper or plastic.

16. The specimen collecting and testing device of claim 1, wherein the foam member extends from an end of the handle member a distance of about 25% to about 400% of a mean diameter of the handle or a mean diameter of an uncompressed cross sectional area of the foam member.

17. The specimen collecting and testing device of claim 1, wherein at least a portion of the housing comprises a transparent material such that the test membrane can be viewed through the portion of the housing.

18. The specimen collecting and testing device of claim 1, wherein at least a portion of the housing is removable, such that the test membrane or sample collecting strip can be viewed or removed through the removable portion of the housing.

19. The specimen collecting and testing device of claim 1, wherein at least a portion of the housing is open, such that the test membrane or sample collecting strip can be viewed through or removed through the open portion of the housing.

20. The specimen collecting and testing device of claim 1, wherein the at least one test membrane or sample collecting strip is removably positioned within the housing.

21. The specimen collecting and testing device of claim 1 wherein the sample collecting strip is impregnated with preservatives.

22. A method of collecting a sample of fluid specimen for diagnostic testing, the method comprising:
    providing a specimen collecting and testing device including:
        an elongate, hollow housing having a proximal end and a distal end;
        at least one test membrane or sample collecting strip positioned within the housing, the test membrane carrying diagnostic test chemistry;
        a fluid chamber, for holding specimen, positioned adjacent to the test membrane or sample collecting strip;
        an aperture in the fluid chamber positioned adjacent to the test membrane or sample collecting strip;
        at least one elongate handle member, having a proximal end and a distal end, slidably received in the housing; and
        a foam member, for collecting specimen, extending from the proximal end of the handle;
    wetting the foam member with specimen;
    positioning the device vertically with the foam member extending upwards;
    sliding the handle member through the housing, thereby drawing the wetted foam member across the fluid chamber and delivering the collected specimen to the fluid chamber; and positioning the device horizontally so as to level off the specimen in the fluid chamber and allow the specimen to flow through the aperture and onto the test membrane or sample collecting strip.

23. The method of claim 22, wherein the specimen collecting and testing device further comprises a barrier or compression area on the proximal side of the fluid chamber, the method further comprising compressing the foam member by the barrier or compression area, thereby expelling collected specimen which flows downwards into the fluid chamber.

24. The method of claim 22, further comprising the step of removing the test membrane or sample collecting strip from the housing after the delivery of the specimen for further processing.

25. The method of claim 22, wherein the specimen collecting and testing device further includes a backup chamber proximate to the fluid chamber and wherein said step of positioning the device horizontally so as to level off the specimen in the fluid chamber further comprises allowing specimen in excess to the capacity of the fluid chamber to flow into the backup chamber.

26. The specimen collecting and testing device of claim 1, wherein the elongate handle member is slidably received in the same hollow portion of the housing as the test membrane or sample collecting strip is positioned.

27. A specimen collecting and testing device comprising:
  a. a sample collecting mechanism comprising;
    an elongate, hollow housing having a channel, a proximal end and a distal end and a hollow portion;
    an elongate handle member slidably mounted within the channel;
    a foam member for collecting specimen extending from the proximal end of the handle; and
  c. a sample testing mechanism comprising:
    at least one test membrane or sample collecting strip carrying diagnostic test chemistry positioned within the hollow portion of the housing; and
    a fluid chamber, for holding specimen received from the foam member, within the hollow portion of the housing, the fluid chamber being adjacent to the channel and to the test membrane or sample collecting strip.

28. The specimen collecting and testing device of claim 27 further comprising a sample extraction mechanism comprising: the elongate hollow housing, whereby when the handle is drawn through the housing, collected specimen is extracted from the foam member and deposited onto the test membrane or sample collecting strip.

29. The specimen collecting and testing device of claim 27, wherein the elongate handle member and housing are coaxial.

30. A specimen collecting and testing device comprising:
  an elongate, hollow housing having a proximal end and a distal end;
  an elongate handle member having a proximal end and a distal end, the handle member slidably mounted within the housing;
  the elongate handle member and housing being coaxial;
  a foam member for collecting specimen extending from the proximal end of the handle;
  at least one test membrane or sample collecting strip carrying diagnostic teat chemistry positioned within to housing, and
  a fluid chamber for holding specimen positioned adjacent to the test membrane or sample collecting strip, the fluid chamber having an aperture, whereby specimen collected by the foam member is deposited into the fluid chamber, through the aperture and onto the test membrane.

31. A specimen collecting and testing device comprising:
  an elongate, hollow housing having a channel, a proximal end and a distal end and a hollow portion;
  at least one test membrane or sample collecting strip positioned within the hollow portion of the housing, the test membrane carrying diagnostic test chemistry;
  a fluid chamber, for holding specimen, positioned adjacent the channel within the hollow portion of the housing and adjacent to the test membrane or sample collecting strip;
  at least one elongate handle member, having a proximal end and a distal end, slidably received in the channel of the housing; and
  a foam member, for collecting specimen, extending from the proximal end of the handle whereby, when the handle is drawn through the channel, collected specimen is deposited from the foam member into the fluid chamber and onto the test membrane or sample collecting strip.

32. A method of collecting a sample of fluid specimen for diagnostic testing, the method comprising:
  providing a specimen collecting and testing device including:
    an elongate, hollow housing having a channel, a proximal end and a distal end;
    at least one test membrane or sample collecting strip positioned within the housing, the test membrane carrying diagnostic test chemistry;
    a fluid chamber, sized for holding specific volumes of specimen, positioned adjacent to the channel and to the test membrane or sample collecting strip;
    an aperture in the fluid chamber positioned adjacent to the test membrane or sample collecting strip;
    at least one elongate handle member, having a proximal end and a distal end, slidably received in the channel; and
    a foam member, for collecting specimen, extending from the proximal end of the handle;
  wetting the foam member with specimen;
  positioning the device vertically with the foam member extending upwards;
  sliding the handle member through the channel of the housing, thereby drawing the wetted foam member across the fluid chamber and delivering the collected specimen to the fluid chamber;
  positioning the device horizontally so as to level off the specimen in the fluid chamber, and so as to allow specimen in excess of the volume of the fluid chamber to flow out of the fluid chamber; and
  allowing the specimen in the fluid chamber to flow through the aperture and onto the test membrane or sample collecting strip.

33. A specimen collecting and testing device comprising:
  a. a sample collecting mechanism comprising:
    an elongate, hollow housing having a channel, a proximal end and a distal end and a hollow portion;
    an elongate handle member slidably mounted within the channel of the housing;
    a foam member for collecting specimen extending from the proximal end of the handle;

b. a sample holding and metering mechanism comprising:
  a fluid chamber, for holding specimen, positioned adjacent to the channel and to the test membrane or sample collecting strip whereby, when the handle is drawn through the housing, collected specimen is deposited from the foam member into the fluid chamber prior to being deposited onto the test membrane or sample collecting strip; and
c. a sample testing mechanism comprising:
  at least one test membrane or sample collecting strip carrying diagnostic test chemistry positioned within the hollow portion of the housing.

34. A specimen collecting and testing device comprising:

an elongate, hollow housing having a channel a proximal end and a distal end;

an elongate handle member having a proximal end and a distal end, the handle member slidably mounted within the channel of the housing;

the elongate handle member and housing being coaxial;

a foam member for collecting specimen extending from the proximal end of the handle;

at least one test membrane or sample collecting strip carrying diagnostic test chemistry positioned within the housing, and a fluid chamber for holding specimen positioned adjacent to the channel and to the test membrane or sample collecting strip, whereby specimen collected by the foam member is deposited into the fluid chamber, whereby the fluid chamber is sized so as to hold specific volumes of specimen, and whereby only the specific volume of specimen is deposited from the fluid chamber onto the test membrane.

* * * * *